United States Patent [19]

Lohmann

[11] Patent Number: 4,852,987
[45] Date of Patent: Aug. 1, 1989

[54] DEVICE FOR MEASURING EYE LENS OPACITY

[76] Inventor: Wolfgang Lohmann, Petersweiher 20, D-6300 Giessen, Fed. Rep. of Germany

[21] Appl. No.: 105,294
[22] PCT Filed: Nov. 24, 1986
[86] PCT No.: PCT/DE86/00478
§ 371 Date: Sep. 29, 1987
§ 102(e) Date: Sep. 29, 1987
[87] PCT Pub. No.: WO87/03188
PCT Pub. Date: Jun. 4, 1987

[30] Foreign Application Priority Data

Nov. 29, 1985 [DE] Fed. Rep. of Germany ....... 3542167

[51] Int. Cl.$^4$ .......................... A61B 3/10; A61B 5/00
[52] U.S. Cl. .................................. 351/221; 351/214; 128/633
[58] Field of Search ............... 351/214, 221, 246, 213; 128/633

[56] References Cited

U.S. PATENT DOCUMENTS

| | | | |
|---|---|---|---|
| 4,235,529 | 11/1980 | Kawase et al. | 351/214 |
| 4,327,973 | 5/1982 | Raif | 351/213 |
| 4,412,543 | 11/1983 | Vassiliadis et al. | 128/633 |
| 4,523,821 | 6/1985 | Lang et al. | 351/214 |
| 4,569,354 | 2/1986 | Shapiro et al. | 128/665 |

FOREIGN PATENT DOCUMENTS 2922788  12/1979  Fed. Rep. of Germany .

OTHER PUBLICATIONS

Lerman "Altern der Linse", (Aging of the Lens), Symposium ueber die Augenlinse (Symposium on the Eye Lens), Strasbourg, pp. 139-154 (1982).
"Fluorotron Master", Coherent (1982).

Primary Examiner—Rodney B. Bovernick
Assistant Examiner—P. M. Dzierzynski
Attorney, Agent, or Firm—Walter Ottesen

[57] ABSTRACT

The invention is directed to an apparatus for making in vivo measurements of eye lens cloudiness such as caused by cataracta nuclearis. The lens of the human eye has an inherent fluorescence which corresponds to the cloudiness. The apparatus of the invention includes a projecting device for projecting a slit image onto the eye lens with a monochromatic excitation beam having a wavelength lying in the range of 350 nm-500 nm. The light beam excites the fluorescence in the eye lens to produce a fluorescence light. A measuring device measures the fluorescence light in the wavelength range of 380 nm to 650 nm. A signal processing unit analyzes the fluorescence spectrum to determine the wavelength corresponding to a maximum intensity of the fluorescence spectrum. The signal processing unit includes a memory having a scale of values for eye lens cloudiness and stores an empirically determined table of values of the measured parameters corresponding to the scale values. Actual measured parameters are compared to the table of values to determine the degree of eye lens cloudiness.

9 Claims, 2 Drawing Sheets

DEVICE FOR MEASURING EYE LENS OPACITY

FIELD OF THE INVENTION

The invention relates to a process and an apparatus for carrying out the process for in vivo measurement of the degree of eye lens opacity or cloudiness, particularly of cataract a nuclearis.

BACKGROUND OF THE INVENTION

Cataracta nuclearis is a frequently occurring eye lens cloudiness in older persons. In it the density and cloudiness of the central portion of the lens increases as the disease progresses. Parallel therewith a discoloration of the lenses from light yellow to dark brown occurs. These changes in the lens lead to a partial loss of the capacity to see or even to blindness. Despite intensive investigations, to date not much is known about the cause or the molecular mechanism of cataract formation. In Appl. Opt. 10, p.459 ff, it is described that the formation of protein aggregates with high molecular weights are responsible for lens cloudiness. The discoloration, in contrast, is attributed to the presence of photochemically induced chromophores (S. Lerman in "Altern der Linse" (Aging of the Lens), p.139 ff, Symposium ueber die Augenlinse (Symposium on the Eye Lens), Strassburg (1982)).

The diagnosis of lens cloudiness is usually made by means of a conventional slit lamp investigation. Evaluations about localization of the center of mass of the cloudiness as well as the degree of maturity of the cloudiness can hereby be made. Both evaluations are dependent to a substantial extent on subjective estimation of the condition. Up to now there has been in practice no apparatus available which can be used in routine operation for an objective determination of lens cloudiness.

Investigations of the fluorescence intensity of individual chromophores have been carried out using a modified Scheim plug camera. In this method the fluorescence is induced with a relatively wide wavelength range in the UV region (300–400 nm) and the fluorescence intensity is measured at two discrete wavelengths (440 nm and 520 nm). Unfortunately, detailed evaluations of the degree of cataracta nuclearis also cannot be made with this method.

To improve the detection sensitivity of methods for detecting minimal, but significant, changes in biological systems, various labels or tracers have been introduced in recent years. Other than radioactive labels, these are primarily fluorescence labels. All of these labels are foreign to the body and must either be injected or orally administered. Even if they are given only in trace amounts, they still adversely influence the relevant biological system.

For these reasons in recent years fluorophotometry using fluorescein as a label (Firm COHERENT) has been developed for cataract investigations. In addition to the intervention in the biological system, this method has the disadvantage that the inducing wavelength depends on the fluorescence wavelength of the fluorescein, and the patient is not permitted to subject himself to sunlight for an extended period of time after the examination since his eyes have become very light sensitive due to the fluorescein and the possibility of damage cannot be ruled out.

Fluorescein is likewise used for investigation of blood-retina and blood-water barriers or to indicate the microcapillaries of the background of the eye. Despite the above-mentioned objections, it is the accepted method since at present no better processes are available.

Since lens clouding takes place gradually, in most cases the patients in the beginning do not notice the clouding of the lenses. The physician is first sought out in a relatively advanced stage. In no event can the aforementioned methods of examination indicate an exact stage of lens clouding. Usually today four stages are used for its classification, the assignment of which by the treating physician does not always take place clearly. A substantial reason therefor lies in the fact that no quantitative values can be established for the individual stages and thus the assignment occurs subjectively and arbitrarily. For an exact determination of the course of the disease it is therefore absolutely necessary to be able to make quantitative evaluations, i.e. to establish a direct relation of the diagnostic criteria to the changes in the cataract lens. Special value must thereby be placed on early recognition in order to prevent further development of the disease or at least to delay it. The conventional slit lamp examination is much too unsensitive for this.

SUMMARY OF THE INVENTION

The invention is therefore based on the problem of providing a simple process for making a diagnosis with which it is possible to detect even slight lens changes as early as possible and moreover to be able to exactly determine the degree of cataract formation within a scale which describes the lens changes. The process should be able to be carried out with an apparatus which is constructed in large measure from known components which have been proved in eye investigations.

The subject matter of the invention can be brought into context with the following observations made independently of each other, whereby in addition a conclusion can be made about the causes of cataract formation.

In earlier investigations it was determined that with slight anomalies in the human tissue system, an additional signal occurs in the electron spin resonance spectrum of the relevant tissue which can be correlated with the ascorbyl radical. Since in intact biological systems, ascorbic acid (vitamin C) is present almost exclusively in the reduced state, the anomalies under investigation thus relate to a material exchange disturbance which affects the vitamin C redox equilibrium and leads to oxidation of the vitamin C from ascorbic acid via the ascorbyl radical to dehydroascorbic acid. As the illness progresses, the oxidation process predominates, as a consequence of which the dehydroascorbic acid is also oxidized. This leads to oxidative decomposition products of the vitamin C, for example, diketogluconic acid up to methyl glyoxal.

In the investigation of the vitamin C oxidation mechanisms, the interesting observation was made that a vitamin C solution which is transparent when freshly prepared, in the course of time (days to weeks) is discolored from yellow to dark brown and yields a characteristic fluorescence spectrum as the discoloration increases. Cataract lenses undergo a similar discoloration. Since it is known that the lens of the eye contains a high concentration of ascorbic acid, the fluorescence behavior of the lenses was also investigated based on the similar discoloration behavior. It was thereby surprisingly determined that there is an exact parallelism in the fluorescence behavior of cataract lenses and of vitamin C solutions. With monochromatic excitation between 350–500 mn and recording of the fluorescence throughout a specific spectral range up to about 650 nm, freshly produced vitamin C solutions show no fluorescence; this also applies to healthy lenses which indeed at 350 nm excitation exhibit a slight natural fluorescence which does not occur with longer wave excitation, however, and otherwise exhibits no characteristic features. The specific fluorescence first develops further with increasing discoloration and is characteristic of the existing degree of discoloration both with regard to intensity as well as the position (wavelength) of the fluorescence maximum. Since fluorescence measurement is one of the most sensitive methods of measurement, changes in the lenses upon formation of cataracts can be detected at a very early stage, and based on the distribution pattern of the fluorescence intensities, minute differences between the individual cataract stages can be detected with the process according to the invention.

The results found in the investigation of vitamin C solutions allow one to conclude that the increasing development of lens cloudiness and discoloration is also due to increasing oxidation of ascorbic acid. This recognition is the basis of the advantages of the process according to the invention. The patient does not need to be investigated with many fluorescent substances foreign to the body. The primary fluorescence of a natural body substance is measured, the degree of oxidation of which corresponds to the state of development of the cataract. The availability of several fluorescence bands yields further detailed information through comparisons of intensities which surely will be useful in the future for therapeutic purposes, since the fluorescence spectrum likewise indicates the progress and success in treatment. The process is very specific. In the investigated wavelength range (350–500 nm for the excitation; 380–650 nm for the recording) interfering fluorescences hardly occur at all. A concentration as small as about 1 micromole of oxidized vitamin C can be detected.

BRIEF DESCRIPTION OF THE DRAWINGS

The fluorescence spectra for different excitation wavelengths at variously advanced cataract stages are illustrated in FIGS. 1 through 3.

DESCRIPTION OF THE PREFERRED EMBODIMENTS OF THE INVENTION

Figure 1:
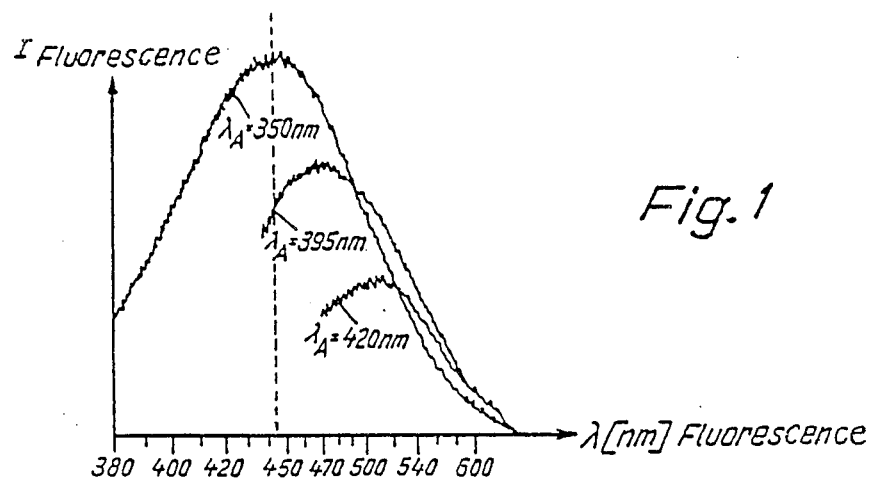

The measurement curves illustrated in FIG. 1 were obtained by measuring a yellowish discolored lens. Clearly marked fluorescence spectra occur for the excitation wavelengths $\lambda_A=350$ nm, $\lambda_A=395$ nm and $\lambda_A=420$ nm. As the excitation wavelength $\lambda_A$ increases, the intensity of the fluorescence spectrum decreases. At longer excitation wavelengths no fluorescence spectra can be detected at this stage of cataract formation. On the other hand, a beginning cataract formation can be recognized from the first appearance of a fluorescence spectrum for $\lambda_A=350$ nm. The wavelength associated with the maximum of the fluorescence spectrum at $\lambda_A=350$ nm lies at 445 nm in this stage. For a lesser degree of cataract formation, the maximum is displaced toward longer wavelengths, as can be determined from the subsequent illustrations.

Figure 2:
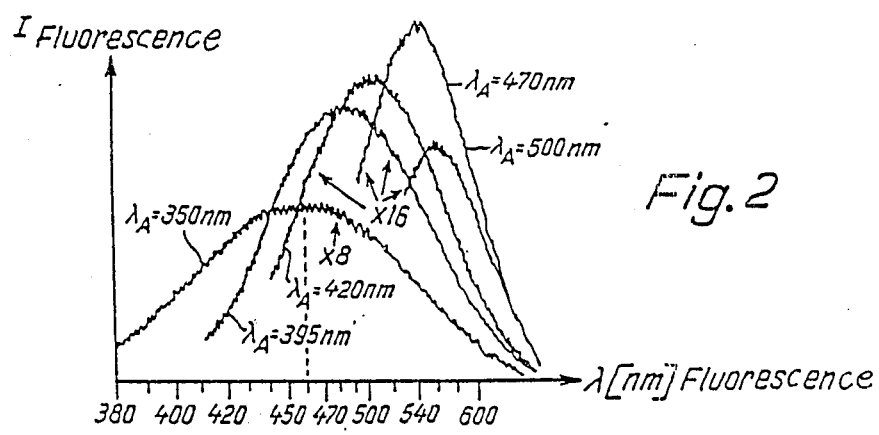

The measurement illustrated in FIG. 2 is caused by an eye lens which is already brownish discolored. The total intensity of the fluorescence strongly increases. For the fluorescence spectrum lying furthest to the left, which belongs to $\lambda_A=350$ nm, the recording height was dampened by a factor of 8 in comparison to FIG. 1. The intensities of the further fluorescence spectra were dampened by a factor of 16 in order to obtain a representation comparable to FIG. 1. Noteworthy is the excitation of the longer wavelength fluorescence spectra at $\lambda_A=470$ nm and $\lambda_A=500$ nm, the intensities of which far exceed those of the fluorescence spectra excited by shorter wavelengths. The maximum of the fluorescence spectrum for $\lambda_A=350$ nm now lies at about 460 nm.

Figure 3:
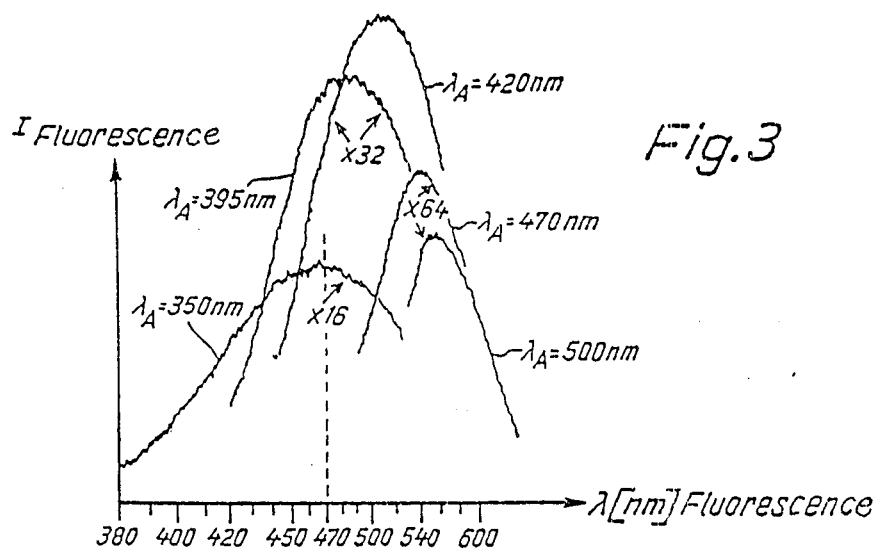

The tendency which already could be seen in FIG. 2 continues in FIG. 3. The measurement illustrated in this figure is caused by an eye lens which is already discolored dark brown. In comparing the illustrated fluorescence spectra it must be kept in mind that the intensity of the fluorescence spectrum excited at $\lambda_A=350$ nm was reduced by a factor of 16 in comparison to the illustration in FIG. 1, while the two following fluorescence spectra at $\lambda_A=395$ nm and $\lambda_A=420$ nm were reduced by a factor of 32 and the two fluorescence spectra at $\lambda_A=470$ nm and $\lambda_A=500$ nm appearing at the right were reduced by a factor of 64 in order to produce a comparable representation within the same figure. The maximum of the fluorescence spectrum at $\lambda_A=350$ nm has been displaced further in the longer wave region to $\lambda=470$ nm.

The measurements illustrated in FIGS. 1 through 3 make the following clear. A beginning cataract formation can be recognized from the fluorescence at $\lambda_A=350$ nm. Through a series of measurements at different degrees of discoloration of cataracta nuclearis a wavelength scale can be established which is correlated with the visually discerned color determinations.

With progressive formation of cataracts, i.e. increasing discoloration, the fluorescence with longer wave excitation sets in gradually and then increases more strongly than that with short wave excitation. Besides the displacement of the fluorescence maximum, each stage of cataract formation is therefore also characterized by the intensity ratios of the fluorescence maxima at different excitation wavelengths. The wavelength scale can therefore be supplemented in an advantageous manner, particularly in the range of already visually discernable cataract formation, by one or more typical intensity ratios. Since the intensity changes corresponding to the illustrations in FIG. 1–3 are substantially clearer than the wavelength displacements of the maxima of the fluorescence spectra, a scale set up following these criteria permits a still finer subdivision for quantitative indication of the degree of cataract formation.

The analog depiction of fluorescence spectra illustrated in FIGS. 1 to 3 can be digitalized with the aid of known electronic circuits and can then be conducted to the memory of a computer for evaluation.

Figure 4:
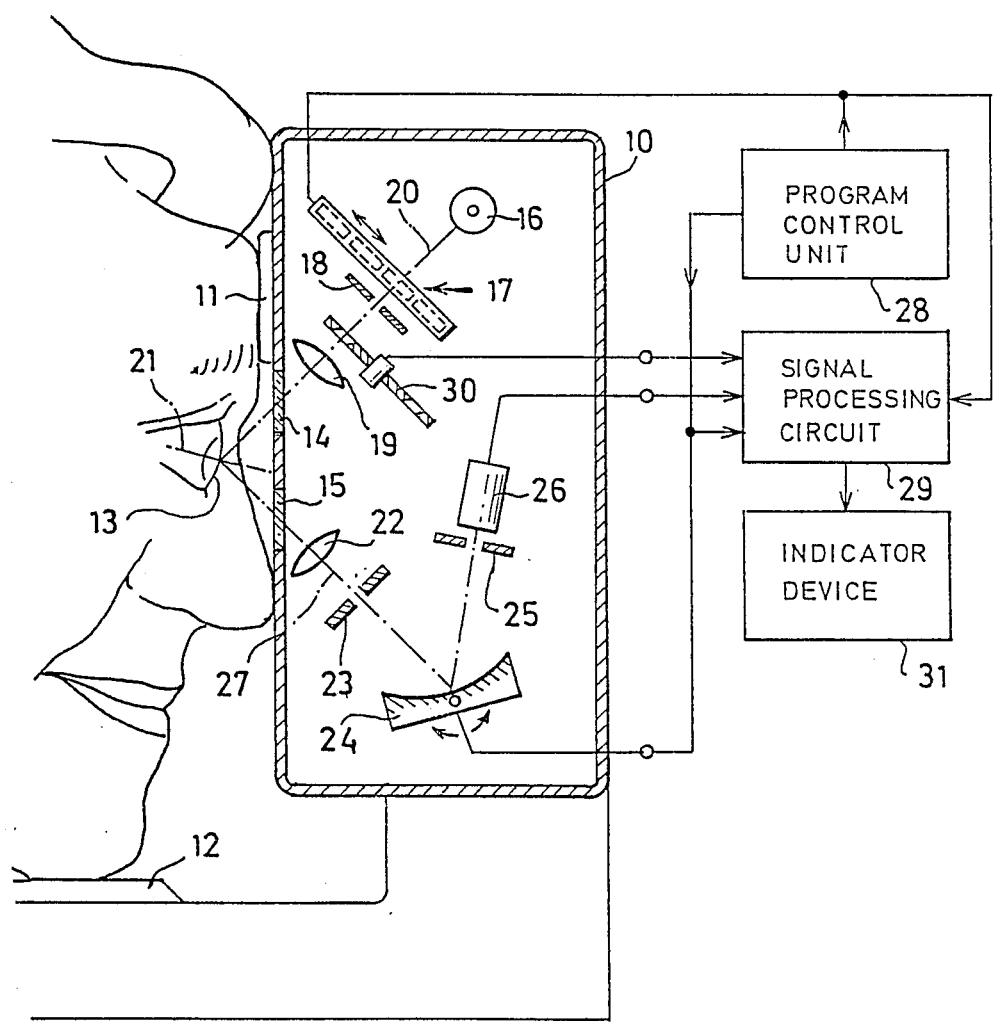
FIG. 4 shows a schematic representation of a suitable measuring device.

In FIG. 4 an apparatus is schematically illustrated which is put together from known components but, however, makes it possible to carry out the process of the invention in a particularly advantageous manner. The optical portion of the measurement device is housed in a housing 10. This is provided with adjustable contact and support surfaces 11,12 on which the head of the patient can be supported so that the eye lens 13 to be examined is located at the intended measurement location.

The housing advantageously has two openings 14,15 through which, on the one hand, a slit image is projected onto the eye lens 13, and, on the other hand, the stimulated fluorescence light is captured. Through a further opening, not shown, or with the aid of suitable beam divider in the illuminating beam path, the position of the slit image on the eye lens can be observed supplementally.

The illuminating beam path contains a light source 16, the emission spectrum of which contains the required excitation wavelengths in sufficient intensity, such as, for example, a xenon high pressure lamp. With the help of a subsequently included monochromizing device (not shown) or a series of interference filters arranged on a slide 17, monochromatic illumination of the slit 18 is produced. The slit is projected via the optics 19 through the opening 14 onto the lens 13 to be examined. The optical axis 20 of the excitation beam path is advantageously at an angle of somewhat under 60 with respect to the axis 21 of the eye lens in order to suppress as much as possible interfering fluorescence from tissues which are not of interest.

The fluorescence light stimulated on the eye lens is captured through the opening 15 via optics 22 and conducted to a recording spectrophotometer. This comprises, for example, an inlet slit 23 and a controllably adjustable bending grate 24 which focuses an image of the inlet slit 23 onto an outlet slit 25. A photoelectric detector 26 is arranged behind the outlet slit 25. The optical axis 27 of the detector beam path is advantageously at an angle of less than 90° with respect to the optical axis 20 of the excitation beam path. The plane extending between the excitation beam path and the detector beam path can be arranged at a desired angle with respect to the eye lens.

The adjustment of the filter slide 17 is advantageously effected through a motor (not shown) with the help of a program control unit 28. It can also take place manually, however. The bending grate 24 for receiving the fluorescence spectrum is also advantageously adjusted by a motor, whereby the spectral region to be captured is likewise prescribed through the program control unit 28.

The signal given off by the photoelectric detector 26 is conducted to a signal processing circuit 29 with a computer for evaluation. For better suppression of the excitation light in the detector beam path and to improve the signal/noise ratio in the measurement signal, a chopper 30 is inserted in the excitation beam path. The evaluation of the signal is controlled with the interrupter frequency of the chopper 30 so that the fluorescence signal is received only during the time in which the excitation beam path is interrupted.

Through the supplemental input of the program control signals for the excitation filter position and the recording of the fluorescence spectrum in the signal processing circuit 29, an automatic measurement operation is possible for objective determination of the degree of cataract formation in the eye lens. The computer associated with the circuit 29 determines the position and intensity of the maxima of the recorded fluorescence spectra, derives the intensity ratios of the wavelengths $\lambda_{Max}$, compares them with the scale defining the degree of cataract formation, and depicts the resulting value on an indicator device 31.

I claim:

1. An apparatus for making an in vivo measurement of eye lens cloudiness such as caused by cataracta nuclearis, the eye lens having an inherent natural fluorescence corresponding to the cloudiness, the apparatus comprising:

a device for positioning the head of the patient so as to place the eye in a predetermined fixed position desirable for making the in vivo measurement;

a projecting device for projecting a slit image onto the eye lens, the projecting device including:

a light source for generating a monochromatic excitation beam of light defining an excitation beam axis and having a wavelength $\lambda_A$ lying in the range of 350 nm to 500 nm;

imaging means arranged in said beam for forming the slit image; sand optic means for focusing the slit image on the eye so as to excite the natural fluorescence in the eye lens to produce a fluorescence light defining a fluorescence light axis;

a measuring device for measuring said fluorescence light, the measuring device including:

a recording spectrophotometer for recording a fluorescence spectrum in the wavelength range of 380 nm to 650 nm which is longer than said excitation wavelength $\lambda_A$;

optic directing means for receiving said fluorescence light from the eye lens and directing the same to said recording spectrophotometer; and, signal processing means for analyzing the fluorescence spectrum recorded by said recording spectrophotometer to determine the wavelength $\lambda_{max}$ corresponding to the maximum intensity I of said recorded fluorescence spectrum; said signal processing means including:

a memory having a scale of values for eye lens cloudiness and storing an empirically determined table of values of the measured parameters ($\lambda_A$ and $\lambda_{max}$) corresponding to said scale of values; and, comparator means for comparing the actual measured parameters $\lambda_A$, $\lambda_{max}$ to said table of values thereby determining the degree of the eye lens cloudiness.

2. The apparatus of claim 1, comprising: program control means for successively setting two different excitation wavelengths ($\lambda_{A1}$ and $\lambda_{A2}$) and initiating the analysis of the spectra corresponding to said excitation wavelengths by said signal processing means which determines the wavelengths ($\lambda_{max1}$ and $\lambda_{max2}$) corresponding to the maximum intensities ($I_1$ and $I_2$) and forms an intensity ratio ($I_1/I_2$) from said maximum intensities ($I_1$ and $I_2$); and, said table of values stored in said memory also including empirically determined intensity ratios for corresponding excitation wavelengths.

3. The apparatus of claim 2, wherein: a third excitation wavelength $\lambda_{A3}$ is provided having a fluorescence spectrum with a maximum intensity $I_3$; said program control means successively sets the three excitation wavelengths ($\lambda_{A1}$, $\lambda_{A2}$, $\lambda_{A3}$) and said signal processing means forms intensity ratios $I_1/I_2$ and $I_2/I_3$ from said maximum intensities ($I_1$, $I_2$, $I_3$) corresponding thereto; and, said table of values is supplemented with said intensity ratios.

4. The apparatus of claim 3, wherein: at least one of the wavelengths 350 nm, 395 nm, 420 nm, 420 nm or 500 nm acts as the excitation wavelength $\lambda_A$; and, the fluorescence spectra corresponding to said wavelengths $\lambda_A$ lie in the wavelength regions 380–650 nm, 430–650 nm, 460–650 nm, 490–650 nm and 520–650 nm, respectively.

5. The apparatus of claim 4, said measuring device including a circuit arrangement for digitalizing the fluorescence spectra measured by the spectrophotometer.

6. The apparatus of claim 1, comprising: control circuit means for adjusting the intensity of the excitation beam of light in dependence on the intensity of the fluorescence light.

7. The apparatus of claim 1, wherein the eye lens defines an eye lens axis; and, said excitation beam axis being inclined with respect to said eye lens axis and said fluorescence light axis so as to cause interfering fluorescence excited in tissue layers lying in front of and in back of the eye lens to be reduced as far as possible.

8. The apparatus of claim 1, said light source including a plurality of narrow band interference filters individually placeable into the path of said excitation beam for producing the monochromatic illumination.

9. The apparatus of claim 1, said projecting device including: a chopper for periodically interrupting said excitation beam and wherein the signal evaluation is controlled with the interrupter frequency of the chopper so that he fluorescence spectrum is recorded only during the time in which the excitation beam of light is interrupted.

* * * * *

UNITED STATES PATENT AND TRADEMARK OFFICE
CERTIFICATE OF CORRECTION

PATENT NO. : 4,852,987

DATED : August 1, 1989

INVENTOR(S) : Wolfgang Lohmann

It is certified that error appears in the above-identified patent and that said Letters Patent is hereby corrected as shown below: Title page:

In the Abstract, line 10: delete "fluorescence" and substitute -- fluorescent -- therefor.

In the Abstract, line 11: delete "fluorescence" and substitute -- fluorescent -- therefor.

In column 1, line 8: delete "cataract a" and substitute -- cataracta -- therefor.

In column 1, line 40: delete "Scheim plug" and substitute -- Scheimpflug -- therefor.

In column 3, line 4: delete "350-500 mn" and substitute -- 350-500 nm -- therefor.

In column 3, line 29: delete "many" and substitute -- any -- therefor.

UNITED STATES PATENT AND TRADEMARK OFFICE
CERTIFICATE OF CORRECTION

PATENT NO. : 4,852,987
DATED : August 1, 1989
INVENTOR(S) : Wolfgang Lohmann

It is certified that error appears in the above-identified patent and that said Letters Patent is hereby corrected as shown below:

In column 4, line 63: delete "however,".

In column 5, line 7: insert -- a -- between "of" and "suitable".

In column 5, line 22: delete "60" and substitute -- 60° -- therefor.

In column 6, line 16: delete "sand" and substitute -- and, -- therefor.

In column 6, line 66: delete "420 nm", second occurrence, and substitute -- 470 nm -- therefor.

Signed and Sealed this

Fifteenth Day of May, 1990

Attest:

HARRY F. MANBECK, JR.

*Attesting Officer*     *Commissioner of Patents and Trademarks*